(12) United States Patent
Halseth et al.

(10) Patent No.: US 6,398,743 B1
(45) Date of Patent: Jun. 4, 2002

(54) MEDICAL DEVICE FOR INSERTING A GUIDE WIRE HAVING A RETRACTABLE NEEDLE

(75) Inventors: Thor R. Halseth, Simi Valley; John M Barker, Ventura; Michael J. Botich, Oxnard, all of CA (US)

(73) Assignee: MDC Investment Holdings, Inc., Wilmington, DE (US)

( * ) Notice: Subject to any disclaimer, the term of this patent is extended or adjusted under 35 U.S.C. 154(b) by 0 days.

(21) Appl. No.: 09/628,180

(22) Filed: Jul. 28, 2000

(51) Int. Cl.⁷ ................................................. A61B 5/00
(52) U.S. Cl. ...................... 600/585; 600/434; 600/573; 606/167; 604/164.12
(58) Field of Search ................................. 600/564, 573, 600/576, 581, 585, 434, 435; 606/167, 181; 604/110, 164.12, 198, 171

(56) References Cited

U.S. PATENT DOCUMENTS

| | | |
|---|---|---|
| 4,676,249 A | 6/1987 | Arenas et al. |
| 4,787,891 A | 11/1988 | Levin et al. |
| 4,850,960 A | 7/1989 | Grayzel |
| 4,874,382 A | 10/1989 | Lindemann et al. |

(List continued on next page.)

*Primary Examiner*—John P. Lacyk
*Assistant Examiner*—Charles Marmor, II
(74) *Attorney, Agent, or Firm*—Dann, Dorfman, Herrell and Skillman; Stephen H. Eland

(57) ABSTRACT

A needle-bearing medical device is provided for inserting a guide wire. After use the needle is shielded to render the contaminated needle safe to prevent inadvertent needle sticks. The device includes a housing and a needle having a sharpened tip. A biasing element biases the needle toward a position in which the sharpened tip is shielded. A connector is provided for attaching a fluid collection device to the guide wire insertion device, if desired. A guide is configured for guiding the guide wire through the port and into the needle. A method is also provided for using the medical device, in which the needle is inserted vascularly into a patient. A fluid collection device is attached to the connector of the device and blood is drawn into the fluid collection device to ensure that the needle is properly positioned within a vein or artery of the patient. A guide wire is then inserted into the patient through the device and the needle is retracted to shield the needle. In one embodiment, the device includes a second port through which the guide wire is inserted while the fluid collection device is attached to the insertion device. The device may also include a shield configured for vascular insertion, which shields the needle after the needle is retracted.

28 Claims, 4 Drawing Sheets

U.S. PATENT DOCUMENTS

| | | |
|---|---|---|
| 4,886,067 A | 12/1989 | Palermo |
| 4,886,500 A | 12/1989 | Lazarus |
| 4,900,307 A | 2/1990 | Kulli |
| 4,904,242 A | 2/1990 | Kulli |
| 4,917,102 A | 4/1990 | Miller et al. |
| 4,950,252 A | 8/1990 | Luther et al. |
| 4,955,862 A | 9/1990 | Sepetka |
| 5,046,508 A | 9/1991 | Weissler |
| 5,116,353 A | 5/1992 | Green |
| 5,129,884 A * | 7/1992 | Dysarz ................ 600/576 |
| 5,163,911 A | 11/1992 | Sirimanne et al. |
| 5,217,435 A | 6/1993 | Kring |
| 5,290,244 A | 3/1994 | Moonka |
| 5,295,974 A * | 3/1994 | O'Laughlin ................ 604/198 |
| 5,314,503 A | 5/1994 | Bobrove et al. |
| 5,318,585 A | 6/1994 | Guy et al. |
| 5,330,432 A | 7/1994 | Yoon |
| 5,360,410 A | 11/1994 | Wacks |
| 5,366,441 A | 11/1994 | Crawford |
| 5,376,075 A | 12/1994 | Haughton et al. |
| 5,395,337 A | 3/1995 | Clemens et al. |
| 5,125,718 A | 6/1995 | Tay et al. |
| 5,531,692 A | 7/1996 | Rogers |
| 5,695,475 A | 12/1997 | Best, Jr. et al. |
| 5,695,479 A * | 12/1997 | Jagpal ................ 604/264 |
| 5,702,367 A * | 12/1997 | Cover et al. ................ 604/110 |
| 5,735,813 A * | 4/1998 | Lewis ................ 604/43 |
| 5,749,857 A | 5/1998 | Cuppy |
| 5,788,654 A | 8/1998 | Schwager |
| 5,800,395 A * | 9/1998 | Botich et al. ................ 604/110 |
| 5,846,226 A | 12/1998 | Urmey |
| 5,871,470 A | 2/1999 | McWha |
| 5,882,342 A | 3/1999 | Cooper et al. |
| 5,919,172 A | 7/1999 | Golba, Jr. |
| 5,935,108 A | 8/1999 | Katoh et al. |
| 5,935,113 A * | 8/1999 | Dysarz ................ 604/263 |
| 5,989,220 A * | 11/1999 | Shaw et al. ................ 604/110 |
| 6,050,976 A | 4/2000 | Thorne et al. |
| 6,077,244 A * | 6/2000 | Botich et al. ................ 604/110 |
| 6,099,504 A | 8/2000 | Gross et al. |
| 6,126,641 A * | 10/2000 | Shields ................ 604/192 |
| 6,162,195 A | 12/2000 | Igo et al. |

\* cited by examiner

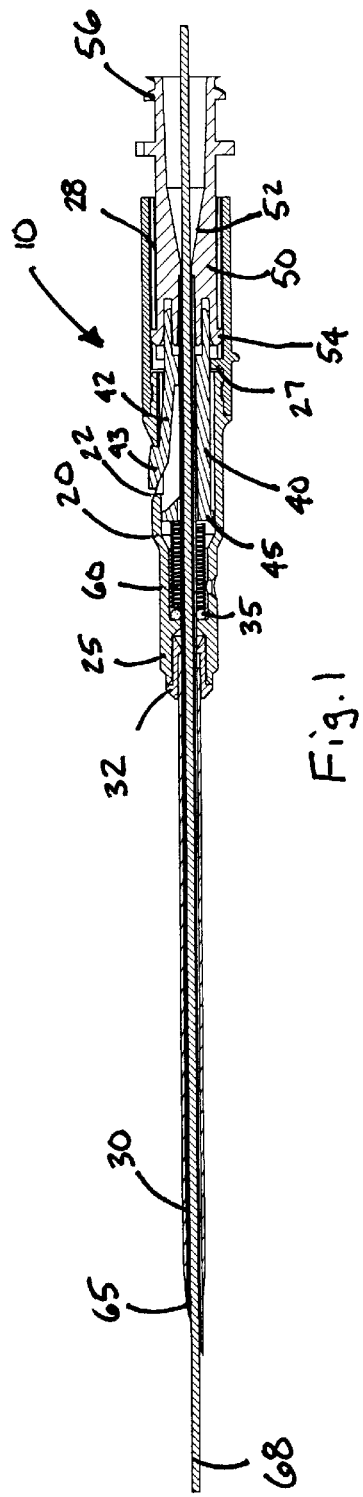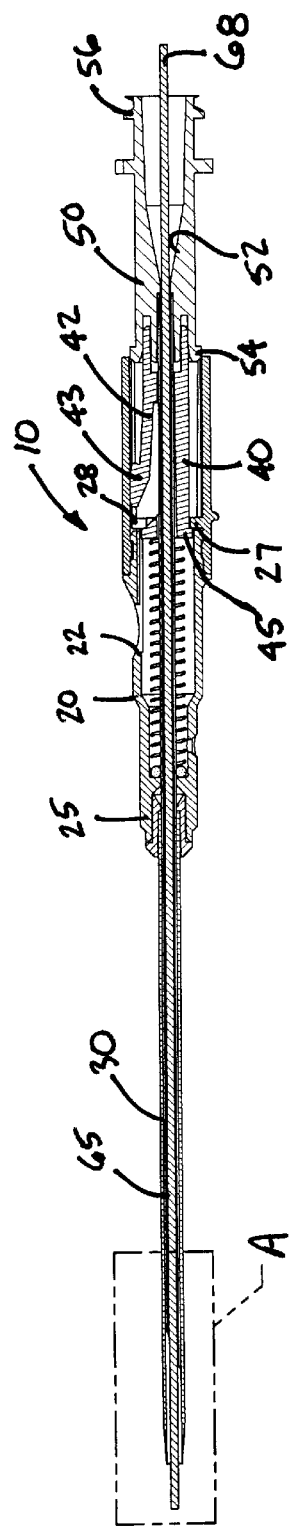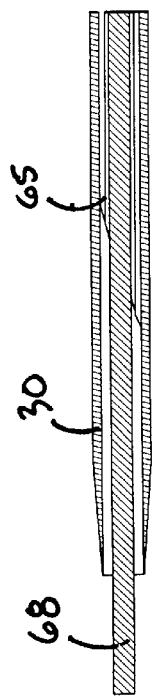

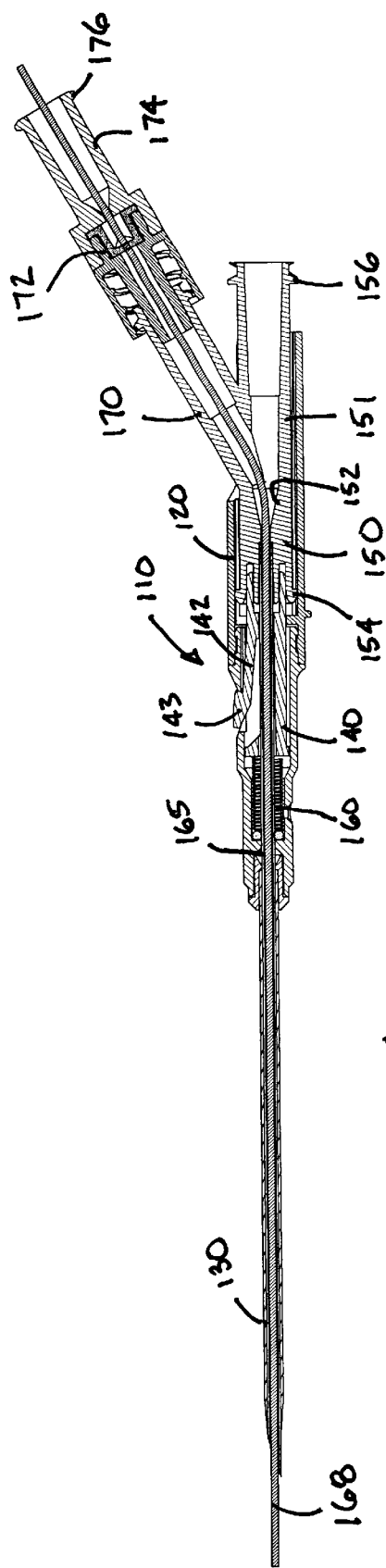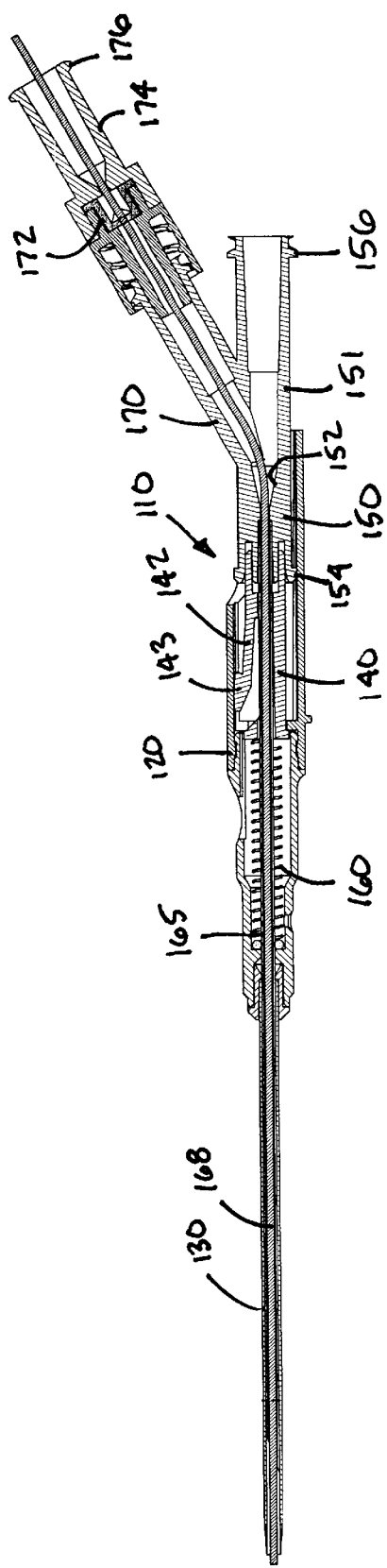
Fig. 4
Fig. 5

MEDICAL DEVICE FOR INSERTING A GUIDE WIRE HAVING A RETRACTABLE NEEDLE

FIELD OF INVENTION

The present invention relates to medical devices for inserting a guide wire into a patient. In a particular, the present invention relates to medical devices having a sharpened needle used for introducing a guide wire into a patient. The needle pierces the patient to provide vascular access, and the guide wire is then inserted into the patient through the needle. After use, the sharpened needle is protected against inadvertent contact. More specifically, after use, the needle is retracted so that the sharpened tip of the needle is enclosed within the device.

BACKGROUND

Various types of medical devices employed a needle for piercing the skin of a patient for diagnostic or therapeutic purposes. One such device is a device for introducing a guidewire into a patient. The guidewire is then used to guide a separate element such as an enlarged bore introducer sheath into the patient. Once the guidewire is properly positioned, the insertion device is withdrawn leaving the guidewire in place in the blood vessel. Handling of such medical devices after the needle is withdrawn from the patient can result in transmission of various pathogens, most notably human immune virus (HIV), due to in inadvertent needle stick to medical personnel.

SUMMARY OF THE INVENTION

In light of the foregoing, the present invention provides a method and apparatus for inserting a guide wire into a patient and rendering the device safe after use to prevent inadvertent contact with the contaminated needle. In accordance with one aspect of the invention, a medical device is provided that has a needle having a sharpened tip projecting forwardly from a housing. Prior to use a shield sheaths a portion of the needle so that the sharpened tip projects forwardly from the sheath. After use the sharpened tip is retracted into the shield. A biasing element biases the needle toward the retracted position, and a hub connected with the needle includes a guide for guiding a guide wire into the patient through the needle and a connector for attaching a fluid reservoir to the device.

The present invention also provides a medical device having a needle having a sharpened tip projecting forwardly from a housing. After use, the sharpened tip of the needle is shielded against inadvertent contact. A biasing element is operable to displace the sharpened tip of the needle into the shielded position. The device includes a connector for attaching a fluid collection device to the housing. The connector also includes a first port, and the device includes a second port in fluid communication with the needle. An adapter associated with the second port is configured for receiving and guiding a guide wire through the second port and into the needle.

The present invention also provides a method for inserting a guide wire into a patient using a needle-bearing medical device having first and second ports. According to the method, a needle is inserted into a patient and blood is aspirated through the first port. The needle is retracted so that the sharpened tip of the needle is shielded to protect against inadvertent contact. A guide wire is then inserted into the patient through the second port.

The present invention also provides a method for inserting a guide wire into a patient using a needle-bearing medical device having a port. The needle is inserted into the patient and a fluid reservoir is attached to the port for collecting blood from the patient. The fluid collection device is detached from the port and a guide wire is inserted into the patient through the device. The needle is retracted to shield the needle to prevent inadvertent contact with the contaminated needle.

Accordingly, when configured and used as described above, the present invention provides a safe and effective method for inserting a guide wire into a patient. In addition, the device is designed to improve manufacturing efficiencies thereby reducing the overall cost of the device.

DESCRIPTION OF THE DRAWINGS

The foregoing summary as well as the following description will be better understood when read in conjunction with the figures in which:

FIG. 1 is a cross-sectional view of a medical device having a retractable needle for inserting a guide wire;

FIG. 2 is a cross-sectional view of the medical device illustrated in FIG. 1, illustrating the needle in a retracted position;

FIG. 3 is an enlarged fragmentary cross-sectional view of the portion designated A of the medical device illustrated in FIG. 2;

DETAILED DESCRIPTION OF THE PREFERRED EMBODIMENT

Figure 6:
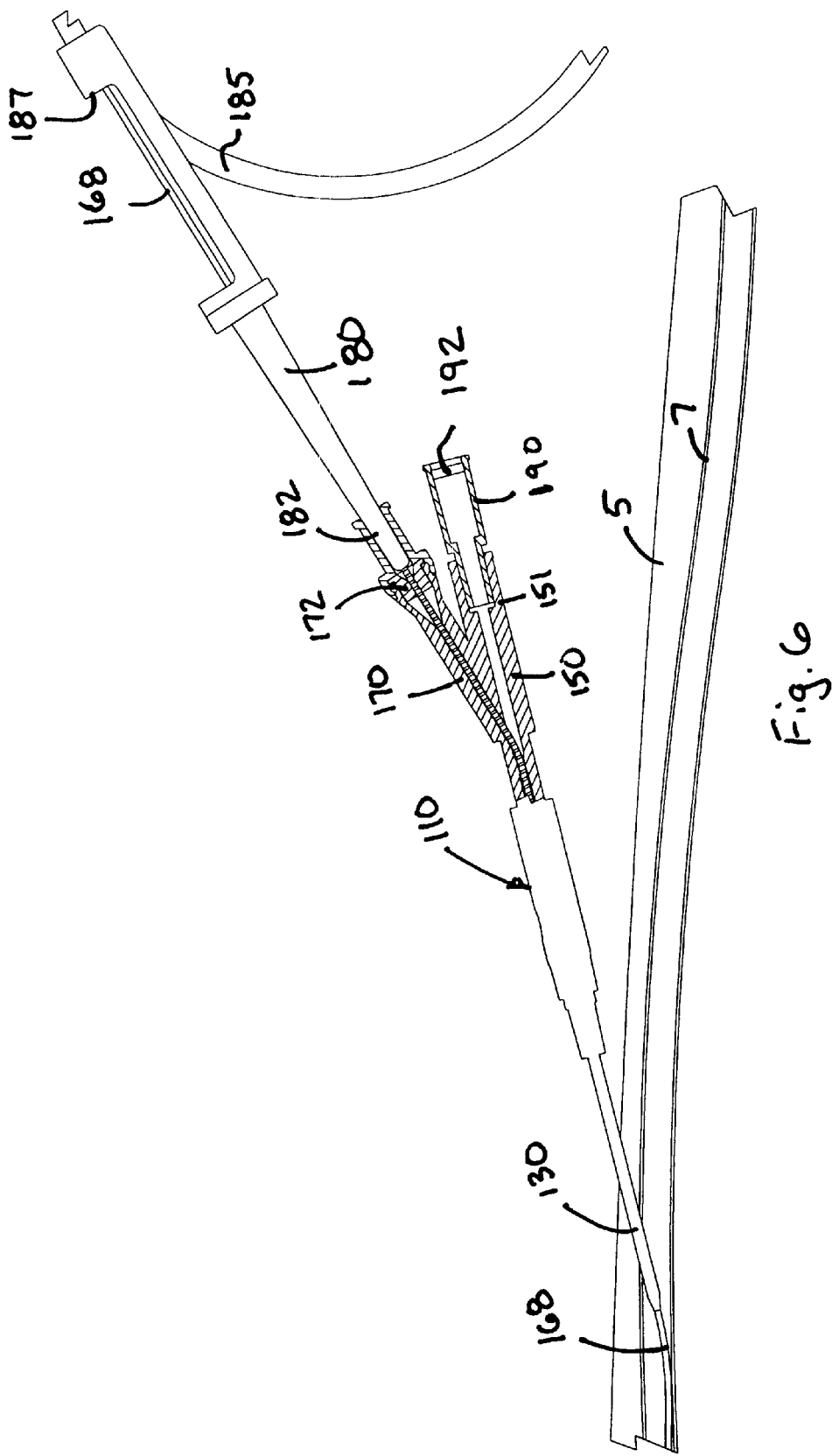
FIG. 6 is a side view partially in section of the medical device illustrated in FIG. 5 in combination with a guide wire feeder, illustrating the device inserted into a patient.

Referring now to the figures in general and to FIG. 1 specifically, a medical device for inserting a guide wire is designated generally 10. The device 10 includes a sharpened needle 65 for inserting the device vascularly. After the needle is inserted into the patient the needle may be retracted into the device 10 so that the sharpened tip of the needle is enclosed. A guide wire can then be inserted into the patient through the needle. After use, the device 10 is withdrawn with the needle safely shielded.

Referring now to FIGS. 1 and 2, the device includes an elongated hollow barrel 20. The needle 65 projects forwardly from the barrel, with a shield 30 surrounding the length of the needle. The needle 65 is attached to a needle hub 40 disposed within the barrel 20. A spring 60 disposed within the barrel biases the needle hub 40 and the attached needle 65 rearwardly toward a retracted position. A needle retainer 42 releasably retains the needle hub against the bias of the spring 60. A port at the rearward end of the device 10 provides access for a guide wire 68, so that the guide wire can be threaded into the patient through the needle 65.

The medical professional using the device 10 can retract the needle by pressing a button 43, which disengages the needle retainer 42. The spring 60 then propels the needle 65 rearwardly so that the sharpened tip of the needle is enclosed within the shield 30. In this way, the contaminated needle 65 is protected against inadvertent contact.

The details of the device will now be explained in greater detail. As shown in FIG. 1, the barrel is a generally cylindrical barrel having a hollow central bore. A locking aperture 22 in the sidewall of the barrel 20 is configured to cooperate with the needle retainer 42 as described further below. The rearward end of the barrel is generally open for receiving the needle hub 40 and a connector hub 50. The forward end of the barrel 20 is generally closed, having a reduced diameter opening through which the needle 65 extends. Preferably, a seal 35, such as an O-ring forms a fluid seal between the reduced diameter opening and the needle 65 to prevent fluid from leaking from the shield 30 into the barrel 20.

A pair of opposing axial slots 28 are formed in the interior surface of the barrel, adjacent the rearward end of the barrel. The slots 28 form a guide track that cooperates with the connector hub 50 to guide the needle 60 during retraction, as is discussed further below. Additionally, the slots 28 cooperate with the connector hub 50 to prevent the button 43 from being twisted relative to the locking aperture 22 when a fluid collection device is attached to the device 10 as is discussed further below. Although the barrel 20 may be formed as a single piece, in the present instance, the barrel is formed in two portions that are snap-fit together. Alternatively, the two portions can be connected by ultrasonic welding or adhesive.

The barrel 20 further includes a flange 27 projecting radially inwardly from the interior surface of the barrel, intermediate the length of the barrel. The flange 27 forms a stop that cooperates with the needle hub 40 to limit rearward displacement of the needle hub, which in turn limits the retraction of the needle.

Referring again to FIGS. 1 and 2, the details of the needle hub 40 are illustrated. The needle hub 40 is generally cylindrical having an internal bore for receiving the needle 65. Preferably, the needle retainer 42 is integrally formed with the needle hub 40. The needle retainer includes an axially elongated radially deformable arm with a latch or button 43. The button 43 is configured to cooperate with the locking aperture 22 in the barrel, to releasably engage the needle hub 40 with the barrel 20. The forward end of the needle hub 40 flares outwardly forming a circumferential flange 45 having an external diameter corresponding to the central bore 24 of the barrel. In this way, as the needle hub 40 is displaced rearwardly during retraction, the flange 45 slides along the interior bore to guide the needle hub.

The needle 65 is operable between a projecting position illustrated in FIG. 1 and a retracted position illustrated in FIG. 2. In the projecting position, the needle projects forwardly from the barrel so that the sharpened tip of the needle is exposed to pierce the patient and guide the shield 30 into the patient. In the retracted position, the sharpened tip of the needle is disposed within the shield 30 to prevent inadvertent contact with the contaminated needle. The spring 60 biases the needle 65 rearwardly toward the retracted position. The needle retainer 42 releasably retains the needle 65 in the projecting position against the bias of the spring 60.

The needle 65 extends through the central bore of the needle hub 40, and through the opening in the barrel tip 25 so that the sharpened tip of the needle projects forwardly from the barrel. The shield 30 is fixedly attached to the barrel tip 25 so that the shield also projects forwardly from the barrel 20. More specifically, the forward end of the barrel 20 forms a cavity or socket. A shield connector 32 is configured to cooperate with the cavity to fixedly attach the shield to the barrel. The shield connector 32 includes an internal bore approximately the same as the external diameter of the shield 30. The shield connector 32 forms an interference fit with the cavity on the barrel, which in turn provides an interference fit between the shield connector and the shield 30, thereby attaching the shield to the barrel. The depth in which the shield connector 32 is inserted into the cavity can be varied so that the length of the shield 30 overlapping the needle 65 can be varied. In this way the length of the needle 65 projecting forwardly from the shield can be controlled during manufacture.

The shield 30 is in the form of a relatively thin-walled cannula, overlying the needle 65 in telescoping relation. Specifically, the interior diameter of the shield is substantially the same as the external diameter of the needle 65. Preferably, the interior diameter of the shield 30 is the same as or several thousandths of an inch larger than the external diameter of the needle so that the needle 65 can readily slide within the shield.

As shown in FIG. 3, the forward end of the shield 30 tapers inwardly forming a thin wall with a feather edge, which provides a smooth transition between the forward end of the shield 30 and the needle 65. In this way, when the needle 65 is inserted into the patient's vein or artery, the overlying shield 30 is also readily inserted into the patient's vein or artery.

A stop limits the rearward travel of the needle hub 40 to limit the distance that the needle 65 is retracted. Specifically, the forward end of the needle hub flares outwardly forming an enlarged head 45. The enlarged head 45 engages the flange 27 on the interior of the barrel 20 when the needle is retracted. In this way, the engagement between the flange 27 and the enlarged head 45 limits the rearward displacement of the needle 65.

Preferably, prior to retraction, the axial distance between the flange 27 and the enlarged head 45 is less than the length of the shield 30 that projects forwardly from the barrel 20. More specifically, preferably the axial distance is less than half the length of the shield that projects forwardly from the barrel 20. It is further preferable that the axial distance be substantially less than one quarter the length of the shield that projects from the barrel. In this way, after retraction, the sharpened tip of the needle is enclosed within the shield 30, rather than being retracted into the barrel 20.

The device 10 further includes elements for impeding re-extension of the needle 65 after retraction, so that the contaminated sharpened tip of the needle is not exposed. Specifically, as shown in FIG. 2, the forward end of the actuator button 43 forms a shoulder that engages the rearward shoulder of the flange 27 on the interior of the barrel. As the needle 65 is retracted, the needle retainer 42 flexes radially outwardly when it is displaced into the larger diameter of the rearward half of the barrel. The rearward edge of the forward half of the barrel forms a lip that operates as a stop engaging the button to prevent the needle from being displaced axially forwardly.

A connector hub 50 attached to the needle hub 40 provides an access port for inserting a guide wire 68 through the device 10 and into the patient. The connector hub 50 includes a central bore in fluid communication with the needle 65. In the present instance, the rearward end of the needle 65 is connected with the connector hub 50.

The connector hub 50 has an open rearward end and preferably forms a connector in the form of a Luer fitting for attaching a medical device, such as a syringe or guide wire feeder as discussed further below. In addition, preferably a lock 56 is formed on the rearward end of the connector hub for locking the separate device to the connector hub. More specifically, preferably, the lock 56 is a threaded Luer lock formed on the exterior of the connector hub.

In addition, a wire guide 52 is formed in the interior of the connector hub 50. The wire guide 52 is formed forward of the open end of the connector hub 50, and includes tapered walls, forming a generally frustoconical transition from the open end of the connector hub to a small diameter opening adjacent to and coaxial with the rearward end of the needle. The wire guide 52 operates similar to a funnel, guiding the wire into the small diameter opening of the needle as the wire is inserted through the large opening at the rearward end of the connector.

The connector hub 50 further includes a pair of opposing guide tabs 54 projecting radially outwardly into engagement with the guide tracks 28 formed in the interior of the barrel 20. The guide tabs 54 cooperate with the guide tracks 28 to guide the needle 65 rearwardly during retraction. In addition, the guide tabs 54 and guide tracks 28 operate as a circumferential lock preventing torque applied to the connector hub from being transferred to the needle retainer 42. In this way, if a fluid collection device, such as a syringe, is attached to the connector hub 50 by threading the syringe onto the connector hub, the torque applied to the connector hub is not transferred to the needle retainer 42, which could cause the needle retainer to break or disengage the locking aperture 22.

In the present instance, the needle hub 40 and connector hub 50 have been described as two separate elements connected together. However, the two elements can alternatively be formed as a single element.

Retracting the needle into the shield rather than the barrel has several benefits. The overall length of the barrel can be reduced because the barrel need not be long enough to accommodate the retracted needle. In addition, the needle 65 provides support for the shield 30 to prevent the shield from collapsing or buckling radially inwardly in response to external forces. For instance, the device 10 is used in conjunction with a guide wire. The guide wire is inserted vascularly into the patient through the needle 65. Prior to inserting the guide wire, and while the device 10 is inserted in the patient, the medical professional may actuate retraction by depressing the button 43. The needle retainer 42 is thereby displaced radially inwardly out of engagement with the barrel, and the spring 60 displaces the needle 65 rearwardly into the retracted position.

As shown in FIG. 2, the needle remains within the shield 30 after retraction. The shield 30 can then be inserted further into the patient without risk of piercing or coring the vein or artery. Depending on the material used for the shield and the wall thickness of the shield, the shield may not have sufficient columnar strength to overcome the resistance of inserting the length of the shield vascularly. In such instances, the needle provides additional rigidity so that the length of the shield can be inserted into the patient. After the length of the shield is inserted into the patient, the guide wire is threaded into the patient through the retracted needle and the shield.

After use, the shield 30 shields the sharpened tip of the needle 65 against inadvertent contact. Preferably, the shield 30 is somewhat flexible. In addition, the shield is preferably formed with sufficient column strength to prevent the shield 30 frown collapsing axially in response to an axial force after retraction. This columnar strength prevents the shield from readily buckling axially after retraction, which could expose the contaminated needle. In other words, the shield 30 is preferably laterally flexible, but is substantially axially incompressible. In the present instance the shield is formed of Teflon. However, a variety of other known plastic materials may be used to form the shield.

Configured in this way, the device 10 is preferably used to insert a guide wire as follows. The needle 65 and shield pierce the skin of a patient and the vein or artery of the patient. Upon inserting the needle vascularly, a flash of blood will flow through the device. The blood flash can be seen, indicating to the medical professional that a vein or artery has been pierced. A medical device, such as a syringe, is then attached to the connector hub 50 and an amount of blood is withdrawn from the patient to ensure that the needle is properly positioned within the patient's vein or artery. Alternatively, the syringe can be attached to the connector hub 50 prior to inserting the needle into the patient. If a syringe is used, the syringe plunger is withdrawn to form a vacuum that draws blood into the syringe barrel. Preferably, approximately 1–3 cc of blood are withdrawn to ensure that the needle is properly positioned.

After the blood is drawn, confirming that the needle 65 is properly positioned, the needle is retracted by depressing button 43. The spring then propels the needle 65 and needle hub 40 rearwardly so that the sharpened tip is shielded. The head 45 of the needle hub engages the flange 27 in the barrel 20 to stop the rearward displacement of the needle. The needle may be retracted so that the sharpened tip is disposed within the barrel. However, as discussed above, preferably, the needle tip is retracted into the shield 30. The shield and the shielded needle are then further inserted into the patient's vein or artery. Preferably, substantially the entire length of the shield is inserted into the patient.

After the shield 30 is inserted into the patient, the guide wire 68 is inserted into the patient. First, the syringe is detached from the connector hub 50. Blood may continue to flow through the connector hub 50 after the syringe is detached. The medical professional may control the flow of fluid by sealing the back end of the connector hub with his or her finger until he or she is ready to feed the guide wire. The guide wire 68 is then fed through the connector hub 50. The tapered surfaces of the wire guide 52 guides the guide wire 68 into the needle 65, so that feeding the wire through the connector hub 50 feeds the wire through the needle and shield 30, into the patient. Once the guide wire is inserted into the needle, the guide wire occludes most of the flow of blood through the device because the internal diameter of the needle is preferably substantially the same as the external diameter of the wire. After the guide wire is inserted into the patient, the device is withdrawn from the patient leaving the guide wire within the patient's vein or artery. Since the contaminated needle 65 is shielded, the device 10 can be safely disposed of without concern of an inadvertent needle stick.

Figure 4:
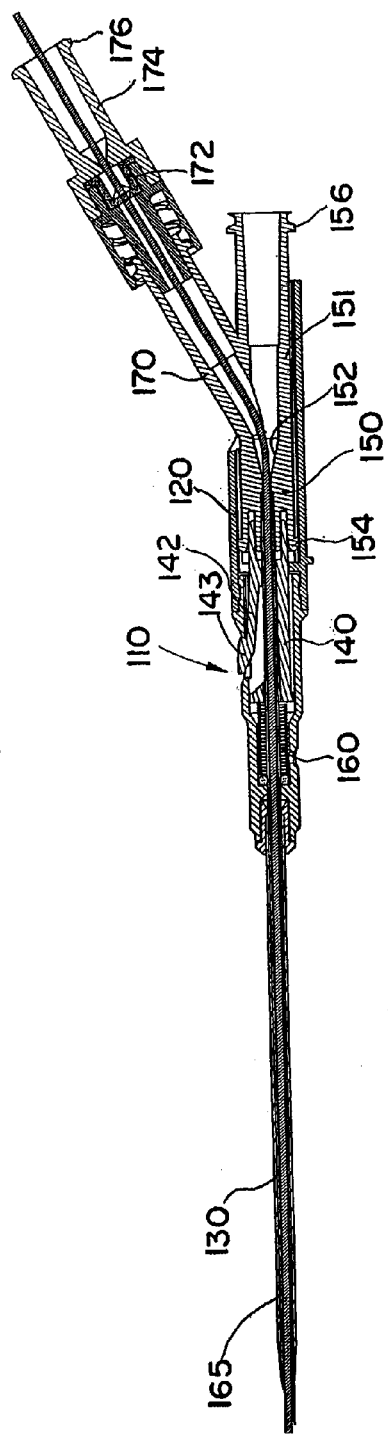
FIG. 4 is a cross-sectional view of an alternate embodiment of a medical device having a retractable needle for inserting a guide wire.
Figure 5:
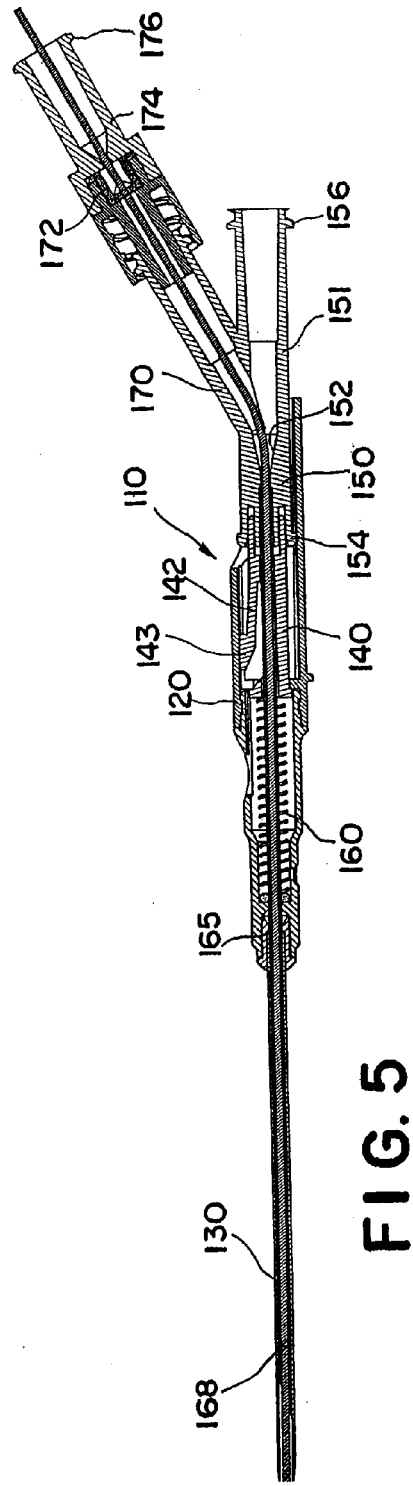
FIG. 5 is a cross-sectional view of the medical device illustrated in FIG. 4, illustrating the needle in a retracted position.
Figure 7:
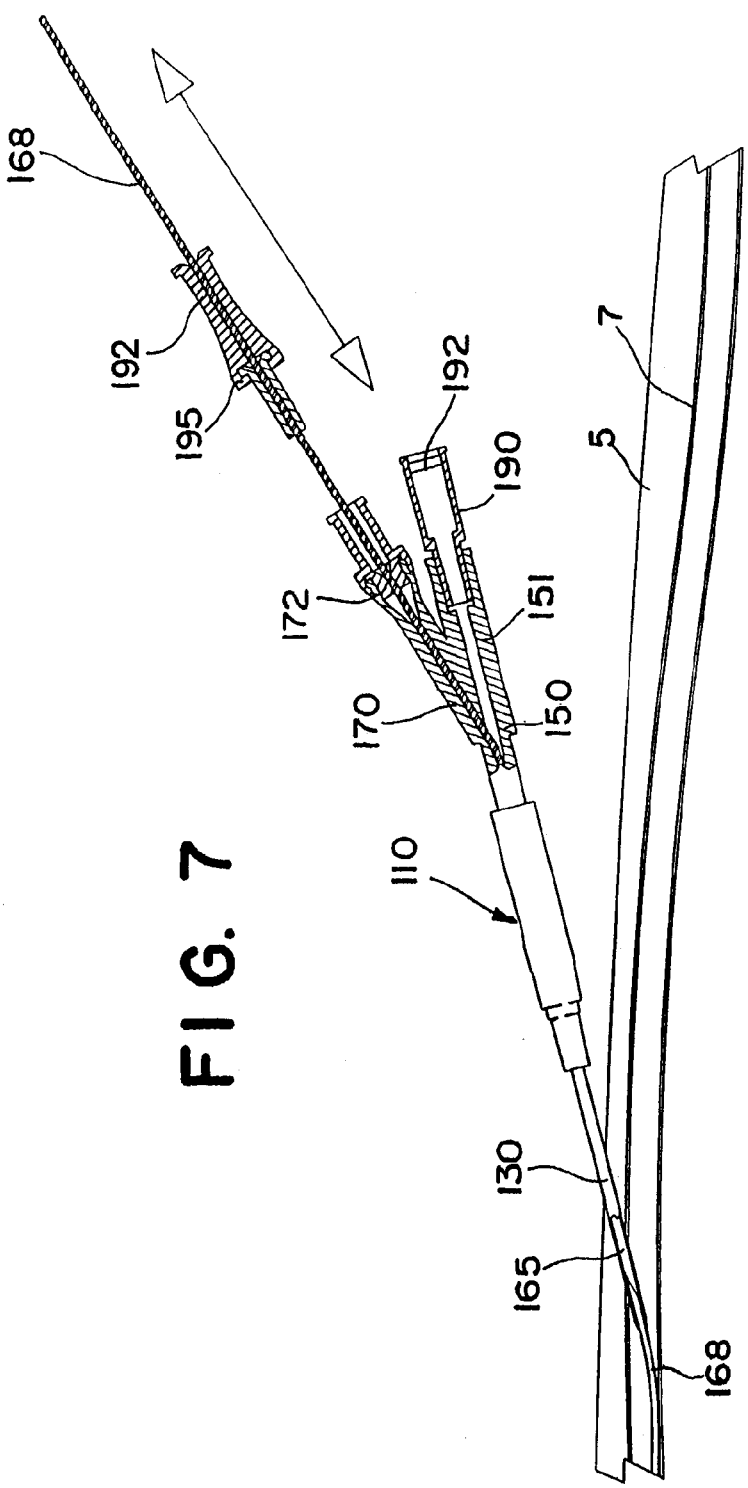

Referring now to FIGS. 4–5, a second embodiment of a guide wire insertion device is designated generally 110. The second embodiment is similar to the first embodiment 10, except that the second embodiment includes a Y-shaped connecting hub 150 having two ports. The two ports allow the device to virtually eliminate blood leakage, thereby providing a "bloodless" procedure as discussed in greater detail below.

The device 110 includes a retractable needle 165 for inserting a guide wire 168. The two ports of the connecting hub 150 allows the medical professional to attach a medical device, such as a syringe, to the first port to draw blood to ensure that the needle is properly placed in a vein, and then leave the syringe attached to the first port to prevent blood from leaking out the first port. The guide wire can then be inserted through the second port and into the patient. In this way, the device 110 substantially reduces or eliminates leakage of blood during the procedure.

Many of the elements of the device 110 are the same or similar to the elements of the first embodiment 10. For instance, the device 110 includes a barrel 120, a needle 165 projecting forwardly from the barrel, a needle shield 130 sheathing the needle, a spring 160 biasing the needle rearwardly, and a needle hub 140 having a needle retainer 142 releasably retaining the needle in the projecting position against the rearward bias of the spring.

However, the barrel 120 has a cut-out or slot for receiving the Y-shaped connector hub 150 having two ports rather than the single port of the connector hub 50 in the first embodiment. The connector hub 150 has a "straight through" portion or leg that is configured similarly to the rearward portion of the connector hub 50 of the first embodiment. The straight through portion 151 is axially aligned with the barrel 120 and the needle 165. The rearward end of the "straight through" leg 151 is generally open, and forms a connector, such as a Luer connector, for attaching a separate medical device, such as a syringe, as described in connection with the first embodiment. A lock 156, such as a threaded Luer lock formed on the straight through leg 151 operates to lock the syringe onto the connector hub 150, sealing the rearward end of the straight through leg.

The second leg of the Y-connector hub 150 is referred to as the Y-leg or feeder leg 170. The feeder leg 170 is transverse the straight through leg 151, and is hollow. The feeder leg 170 can be configured similarly to the straight through leg 151 so that a syringe can be connected to the feeder leg rather than the straight through leg. However, preferably, the feeder leg 170 includes a hemostasis valve 172 that operates as a check valve preventing blood from leaking out the feeder leg, while allowing a guide wire 168 to be inserted into the device 110 through the feeder leg. A connector 174, such as a Luer hub having a Luer lock 176 is preferably connected to the feeder leg 170, rearward of the valve 172. The connector 174 allows a guide wire feeder 180, such as a hoop feeder to be attached to the device, as discussed further below.

In addition, a wire guide 152 is formed in the interior of the Y-connector hub 150. The wire guide may be formed to guide the wire from only one of the legs into the needle. However, preferably, the wire guide 152 is formed forward of the intersection of the enlarged bores of the straight through leg 151 and the feeder leg 170. The wire guide 152 is formed of tapered walls, forming a generally frustoconical transition from the large bores of the straight through leg 151 and the feeder leg 170 to a small diameter opening adjacent to and coaxial with the rearward end of the needle. The wire guide 152 operates similar to a funnel, guiding the wire into the small diameter opening as the wire is inserted into the large opening in either the feeder leg 170 or the straight through leg 151.

Configured in this way, the device 110 is operable to insert a guide wire 168 as follows. The needle 165 and shield pierce the skin of a patient and the vein or artery of the patient. Upon inserting the needle vascularly, a flash of blood will flow through the device. A medical device, such as a syringe, is then attached to the connector hub 150 and an amount of blood is withdrawn from the patient to ensure that the needle is properly positioned within the patient's vein or artery. Alternatively, the syringe can be attached to the connector hub 150 prior to inserting the needle into the patient. If a syringe is used, the syringe plunger is withdrawn to form a vacuum that draws blood into the syringe barrel. Preferably, approximately 1–3 cc of blood is withdrawn to ensure that the needle is properly positioned.

After the blood is drawn confirming that the needle 165 is properly positioned, the needle is retracted by depressing button 143. The spring then propels the needle 165 and needle hub 140 rearwardly so that the sharpened tip is shielded. The head 145 of the needle hub engages the flange 127 in the barrel 120 to stop the rearward displacement of the needle. The needle may be retracted so that the sharpened tip is disposed within the barrel. However, as discussed above, preferably, the needle tip is retracted into the shield 130. The shield and the shielded needle are then further inserted into the patient's vein or artery. Preferably, substantially the entire length of the shield is inserted into the patient.

After the shield 130 is inserted into the patient, the guide wire 168 is inserted into the patient. The guide wire 168 is fed through the feeder leg 170. The tapered surfaces of the wire guide 152 guides the guide wire 168 into the needle 165, so that feeding the wire through the feeder leg 170 feeds the wire through the needle and shield 130, into the patient.

Since the guide wire 168 is not fed through the straight through leg 151, the syringe need not be removed from the Y-connector hub, so that the syringe seals the straight through leg, preventing blood from leaking out the straight through leg. In addition, the valve 172 attached to the feeder leg 170 prevents blood from leaking out the feeder leg as the guide wire is inserted into the patient. In this way, the device 110 is operable to achieve a "bloodless" method of inserting a guide wire into a patient, wherein little or no blood leaks from the device during use. In addition, after use, the sharpened tip of the needle 165 is shielded to prevent inadvertent needle sticks with the contaminated needle.

Figure 7:
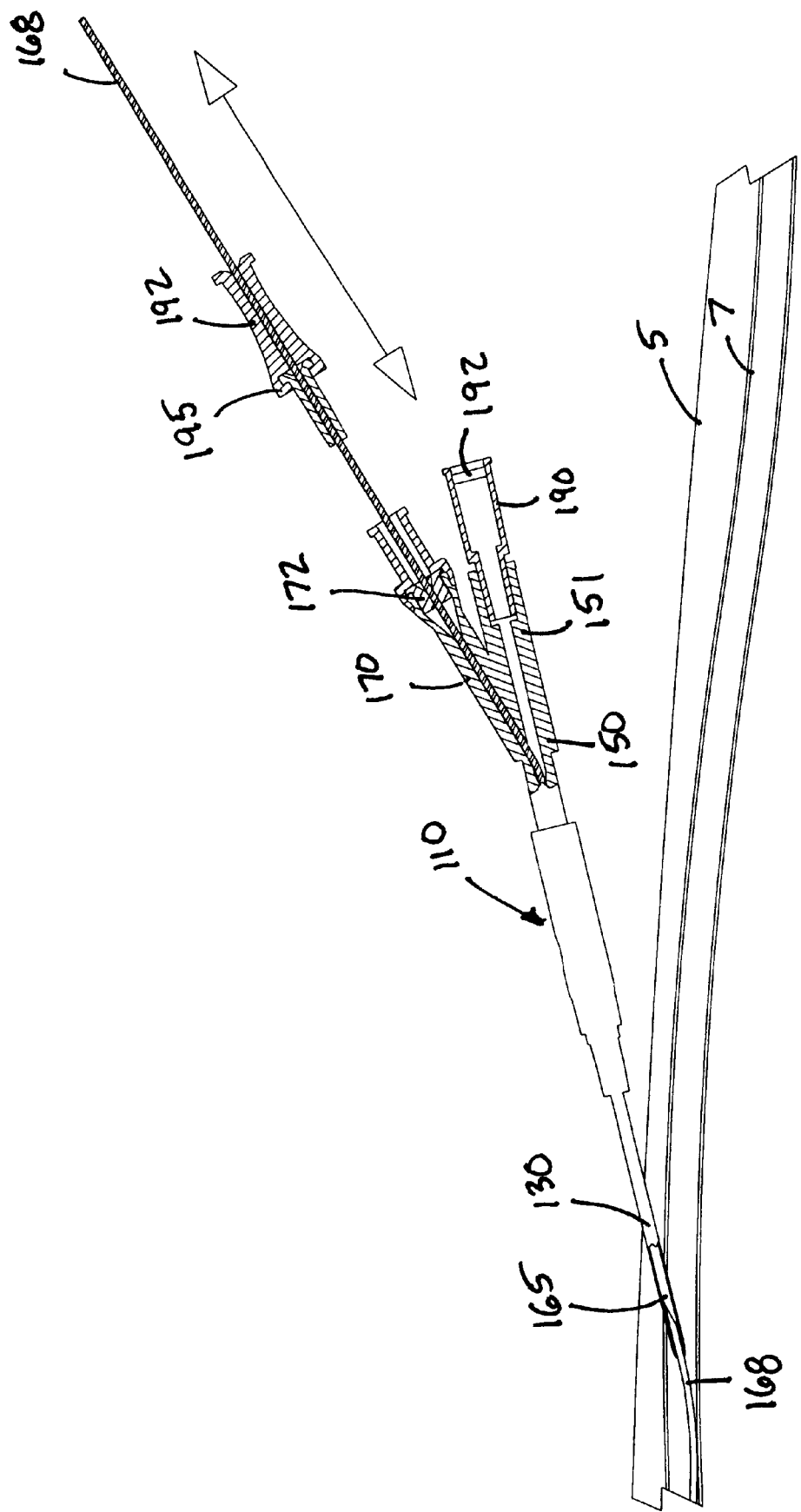
FIG. 7 is a side view partially in section of the medical device illustrated in FIG. 5 in combination with a guide wire gripper, illustrating the device inserted into a patient.

In FIGS. 6–7, the device 110 is illustrated in use in a patient. In FIG. 6, the device 110 is illustrated in connection with a hoop feeder 180. The device is shown after vascular insertion, in which the needle 165 and shield have pierced the patient's skin 5 and vein or artery 7. In FIG. 7 the shield 130 is shown partially broken away with the needle 165 retracted into the shield. In FIGS. 6 and 7, the guide wire 168 is shown being inserted into the patient with the shield 130 only partially advanced into the patient. However, preferably, substantially the entire length of the shield 130 is inserted into the patient prior to inserting the guide wire.

Referring again to FIG. 6, a hoop feeder 180 is shown. The hoop feeder includes a connector 182, such as a male Luer connector, that mates with the Luer connector 174 on the feeder leg 170 to attach the hoop feeder to the device 110. The hoop feeder 180 also includes a length of guide wire 168 sheathed by one or more convolutions of a casing, such as a plastic casing 185. A cut-out or window 187 in the casing 185 provides access to the guide wire 168. The medical professional engages the guide wire 168 in the window 187 to advance the guide wire into the patient through the device.

In FIG. 6, the device 110 is also shown in connection with a dead-end connector 190 attached to the rearward end of the straight through leg 151. Such a dead-end connector can also be attached to the connector hub 50 of the first embodiment. The dead-end connector 190 seals the straight through leg 151 to prevent blood from leaking out the straight through leg. The dead-end connector can be attached to the straight through leg after blood is drawn into a syringe. For such use, the syringe is detached after the blood is drawn, and the dead-end connector is attached in place of the syringe.

Alternatively, and preferably, the dead-end connector 190 includes a hollow interior forming a reservoir for receiving blood. A vent plug 192 in the form of a hydrophobic filter prevents blood from leaking out the back end of the dead-end connector, while allowing air to flow through to prevent the connector from becoming line locked, so that blood can flow into the connector. Preferably the connector 190 is transparent or translucent so that the medical professional can see the blood flowing into the connector.

The dead-end connector 190 can be used in one of several ways. First, the connector 190 can operate as a flash-back chamber. In this manner, the dead-end connector 190 is attached to the straight through leg 151 prior to piercing the patient with the needle 165. After the medical professional pierces the patient with the needle and sees a flash of blood in the connector, the connector is removed and a syringe or similar device is attached to the straight through leg 151 to draw blood to ensure that the needle 165 is properly positioned.

Alternatively, the dead-end connector 190 can operate as the indicator that the needle is properly positioned within the patient's vein or artery. In this manner, if blood flows adequately into the dead-end connector 190, the medical professional retracts the needle and then inserts the shield further into the patient. Since the connector 190 operates as the blood flow indicator, a syringe need not be attached, and the dead-end connector 190 remains attached to the straight through leg 151 to seal it against blood leakage.

Referring again to FIG. 7, the device 110 is illustrated without a feeder, such as the hoop feeder 180 illustrated in FIG. 6. In such use, the medical professional inserts the guide wire 168 by grasping the wire and feeding the wire into the feeder leg. Preferably the medical professional uses a tool to grasp the wire. In one manner, the medical professional grasps the wire with tweezers, advancing the wire with the tweezers, then releasing the wire and regrasping the wire rearward to advance more of the guidewire.

FIG. 7 also illustrates an alternative and preferred tool 195 for grasping the guide wire to feed the guide wire. The gripping tool 195 is formed of a plastic material, and is preferably formed of an elastomeric material so that it is resilient. The gripping tool comprises a pair of jaws 197 for gripping the wire, and a through-bore for receiving the guide wire 168. The through bore is sized slightly larger than the wire diameter so that the wire can readily pass through the gripper 195.

By grasping the sides of the gripper 195, the gripper clamps onto the guide wire 168 so that the medical professional can advance the wire into the patient. After advancing the guidewire 168, the medical professional releases his or her grip of the gripper, which releases the gripper jaws 197 from clamping onto the wire. The medical professional then slides the gripper rearwardly along the wire, then squeezes the gripper to grasp the wire to advance the wire further into the patient. Additionally, preferably the forward portion of the gripper forms a nose configured to cooperate with the open end of the feeder port 170.

The terms and expressions which have been employed are used as terms of description and not of limitation. There is no intention in use of such terms and expressions of excluding any equivalents of the features shown and described or portions thereof. It is recognized, however that various modifications are possible within the scope and spirit of the invention as set forth in the following claims.

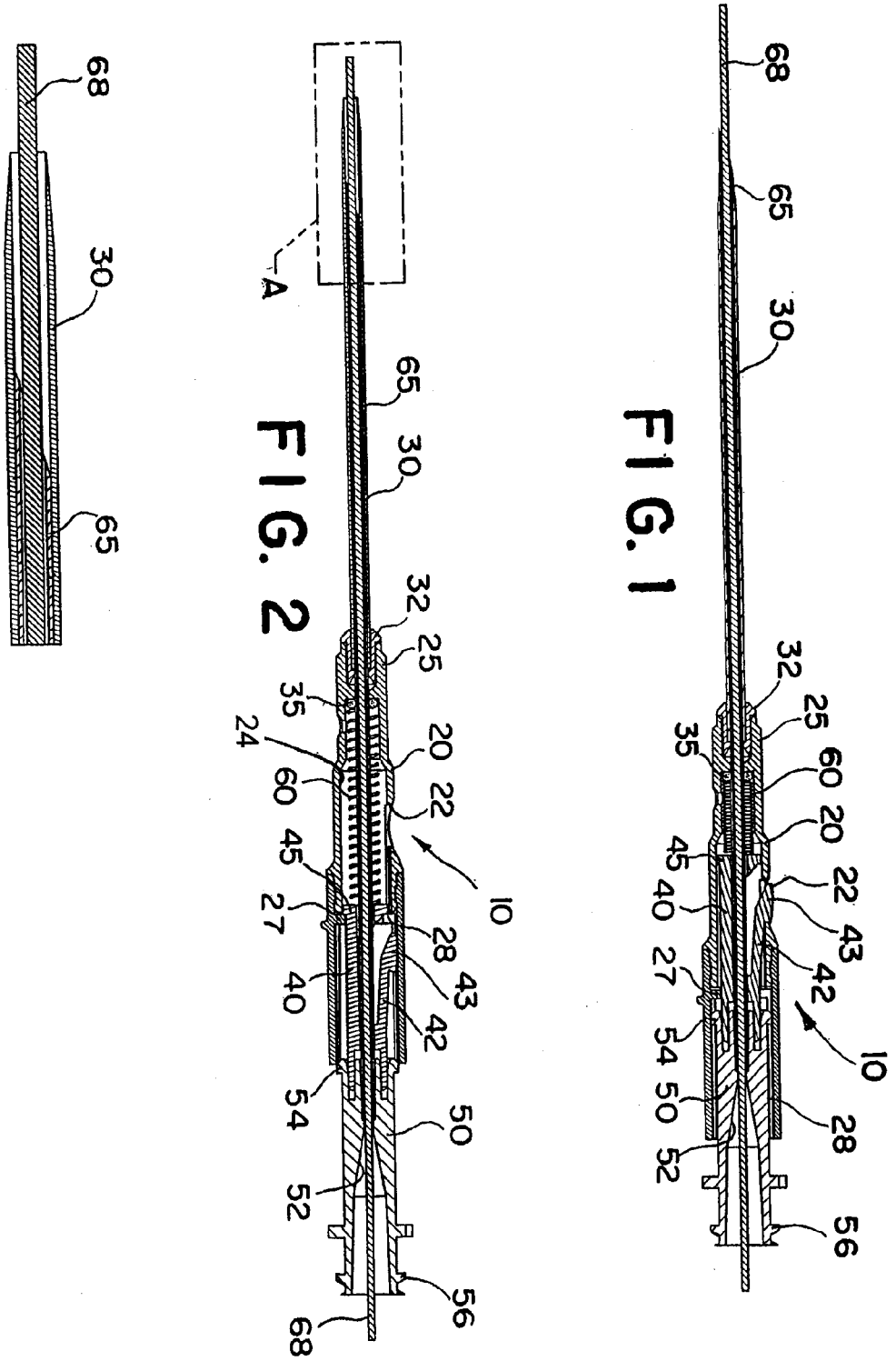

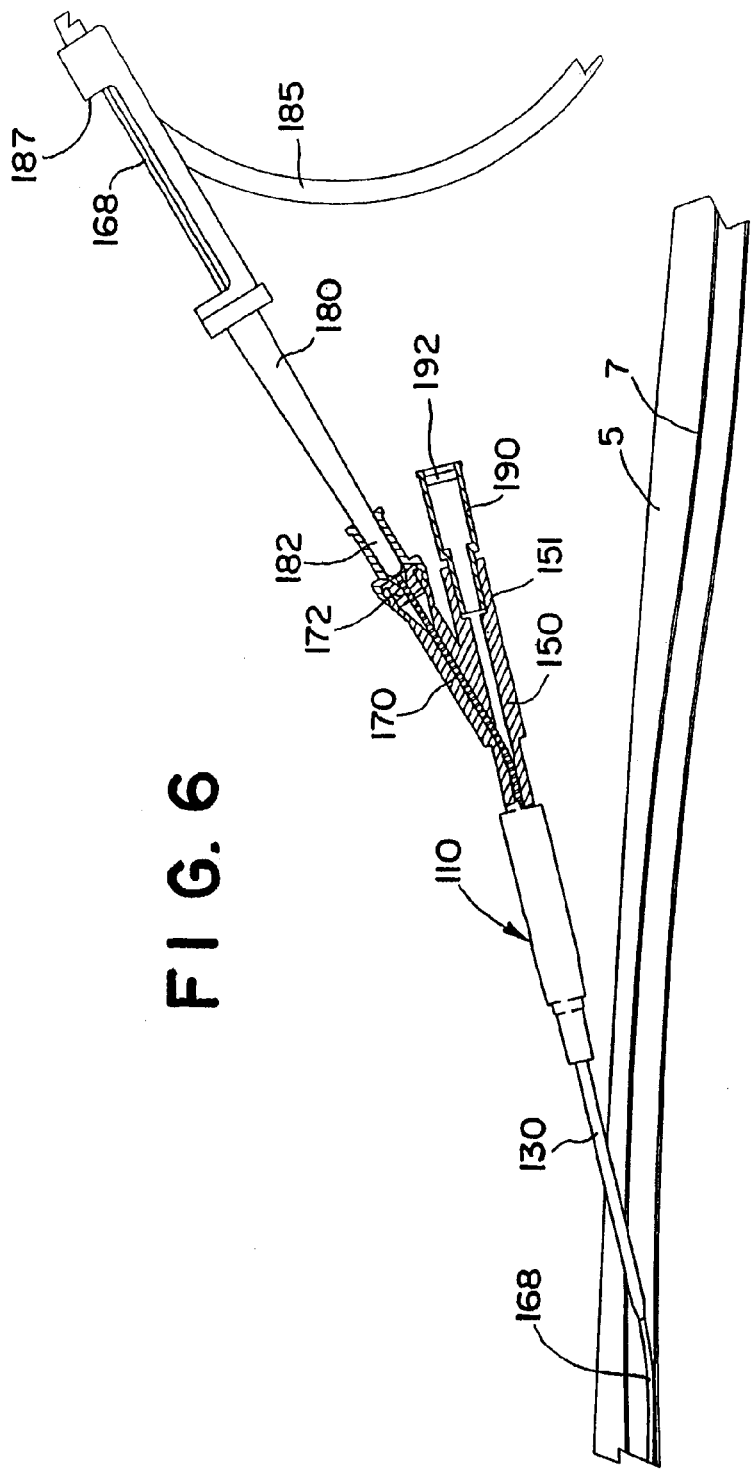

What is claimed is:

1. A method for inserting a guide wire into a patient using a medical device having first and second ports, a shield, and a needle having a sharpened tip, comprising the steps of:
    inserting the needle into the patient;
    allowing blood to flow from the patient through the needle and the first port;
    retracting the needle so that the sharpened tip of the needle is shielded to protect against inadvertent contact;
    inserting the shield into the patient; and
    inserting a guide wire into the patient through the second port.

2. The method of claim 1 wherein the step of allowing blood to flow comprises attaching a fluid collection device to the first port and drawing blood into the fluid collection device.

3. The method of claim 2 comprising the step of releasably connecting the fluid collection device to the first port.

4. The method of claim 2 comprising the step of fixedly connecting the fluid collection device to the first port.

5. The method of claim 2 wherein the guide wire is inserted into the patient while the fluid collection device is attached to the needle-bearing medical device.

6. The method of claim 1 wherein the guide wire is inserted into the patient after the needle is retracted.

7. The method of claim 1 wherein the step of retracting comprises the step of retracting the needle into the needle shield.

8. The method of claim 7 comprising the step of retracting the needle into the shield while the shield is disposed within the patient.

9. A method for inserting a guide wire into a patient using a needle-bearing medical device having a port, comprising the steps of:
    inserting the needle into the patient;
    attaching a fluid collection device to the port;
    collecting blood in the fluid collection device;
    detaching the fluid collection device from the port;
    retracting the needle to shield the needle to prevent inadvertent contact with the contaminated needle; and
    inserting at least a portion of a guide wire into the patient through the medical device after the step of retracting the needle.

10. The method of claim 9 wherein the guide wire is fed into the patient through the port.

11. The method of claim 9 wherein the step of retracting comprises actuating an actuator so that a biasing element retracts the needle.

12. The method of claim 9 wherein the medical device comprises a hub having a connector for attaching the fluid collection device, and the needle is attached to the hub, wherein the step of retracting the needle comprises the step of retracting the hub.

13. The method of claim 9 comprising the step of controlling the flow of fluid flowing through the port.

14. The method of claim 9 comprising the steps of providing a seal over the port and removing the seal prior to attaching the fluid collection device to the port.

15. The method of claim 9 wherein the medical device comprises a shield for shielding the needle, and the method comprises the step of inserting the shield vascularly into the patient.

16. A medical device for inserting a guide wire, comprising:
- a housing;
- a needle having a sharpened tip operable between a projecting position in which the sharpened tip is exposed for piercing a patient, and a retracted position in which the sharpened tip is shielded against inadvertent contact;
- a shield sheathing the needle so that in the projecting position the sharpened tip projects forwardly from the shield and in the retracted position the sharpened tip is disposed within the shield;
- a biasing element biasing the needle toward the retracted position; and
- a hub connected with the needle, comprising:
    - a guide for guiding a guide wire into the patient through the needle; and
    - a connector for attaching a fluid collection device.

17. The medical device of claim 16 wherein the needle has an internal bore and the housing has an enlarged opening that is larger in diameter than the bore of the needle, and the guide comprises a frustoconical portion disposed between the enlarged opening of the housing and the bore of the needle.

18. The medical device of claim 16 comprising a needle retainer releasably retaining the needle in the projecting position against the rearward bias of the biasing element.

19. The medical device of claim 16 wherein the shield is more flexible than the housing.

20. The medical device of claim 16 wherein the shield is substantially cylindrical and the shield has greater lateral flexibility than axial flexibility.

21. The medical device of claim 16 wherein the shield has a tip that convergingly tapers radially inwardly to form a feathered edge.

22. The medical device of claim 16 wherein the shield is substantially incompressible axially.

23. The medical device of claim 16 comprising a guide wire feeder connected to the housing.

24. A medical device for inserting a guide wire, comprising:
- a housing;
- a needle having a sharpened tip operable between a projecting position in which the sharpened tip is exposed for piercing a patient and a retracted position in which the sharpened tip is shielded against inadvertent contact;
- a biasing element for displacing the needle from the projecting position to the retracted position;
- a needle shield configured for vascular insertion and operable to shield the sharpened tip of the needle after the needle is retracted;
- a connector for attaching a fluid collection device to the housing, wherein the connector comprises a first port;
- a second port in fluid communication with the needle; and
- an adapter associated with the second port, configured for receiving and guiding a guide wire through the second port and into the needle;
- wherein after use the biasing element displaces the needle rearwardly into the retracted position.

25. The medical device of claim 24 comprising a second connector for attaching a guide wire feeder to the second port.

26. The medical device of claim 24 comprising a valve sealing the second port, impeding fluid from leaking out the second port while allowing a guide wire to be inserted through the second port.

27. The medical device of claim 24 comprising a wire feeder connected to the second port.

28. The medical device of claim 24 wherein the shield is substantially incompressible axially.

* * * * *

UNITED STATES PATENT AND TRADEMARK OFFICE
CERTIFICATE OF CORRECTION

PATENT NO.   : 6,398,743 B1
DATED        : June 4, 2002
INVENTOR(S)  : Thor R. Halseth et al.

It is certified that error appears in the above-identified patent and that said Letters Patent is hereby corrected as shown below:

Title page,
Title page should be deleted to appear as per attached title page.

Drawings,
The sheets of drawings consisting of figures 1-7 should be deleted to appear as per attached figures 1-7.

Column 5,
Line 67, "frown" should read -- from --;

Signed and Sealed this

Seventeenth Day of December, 2002

JAMES E. ROGAN
*Director of the United States Patent and Trademark Office*

(12) United States Patent
Halseth et al.

(10) Patent No.: US 6,398,743 B1
(45) Date of Patent: Jun. 4, 2002

(54) MEDICAL DEVICE FOR INSERTING A GUIDE WIRE HAVING A RETRACTABLE NEEDLE

(75) Inventors: Thor R. Halseth, Simi Valley; John M Barker, Ventura; Michael J. Botich, Oxnard, all of CA (US)

(73) Assignee: MDC Investment Holdings, Inc., Wilmington, DE (US)

( * ) Notice: Subject to any disclaimer, the term of this patent is extended or adjusted under 35 U.S.C. 154(b) by 0 days.

(21) Appl. No.: 09/628,180

(22) Filed: Jul. 28, 2000

(51) Int. Cl.[7] ............................................... A61B 5/00
(52) U.S. Cl. ................. 600/585; 600/434; 600/573; 606/167; 604/164.12
(58) Field of Search .......................... 600/564, 573, 600/576, 581, 585, 434, 435; 606/167, 181; 604/110, 164.12, 198, 171

(56) References Cited

U.S. PATENT DOCUMENTS

| | | |
|---|---|---|
| 4,676,249 A | 6/1987 | Arenas et al. |
| 4,787,891 A | 11/1988 | Levin et al. |
| 4,850,960 A | 7/1989 | Grayzel |
| 4,874,382 A | 10/1989 | Lindemann et al. |

(List continued on next page.)

*Primary Examiner*—John P. Lacyk
*Assistant Examiner*—Charles Marmor, II
(74) *Attorney, Agent, or Firm*—Dann, Dorfman, Herrell and Skillman; Stephen H. Eland

(57) ABSTRACT

A needle-bearing medical device is provided for inserting a guide wire. After use the needle is shielded to render the contaminated needle safe to prevent inadvertent needle sticks. The device includes a housing and a needle having a sharpened tip. A biasing element biases the needle toward a position in which the sharpened tip is shielded. A connector is provided for attaching a fluid collection device to the guide wire insertion device, if desired. A guide is configured for guiding the guide wire through the port and into the needle. A method is also provided for using the medical device, in which the needle is inserted vascularly into a patient. A fluid collection device is attached to the connector of the device and blood is drawn into the fluid collection device to ensure that the needle is properly positioned within a vein or artery of the patient. A guide wire is then inserted into the patient through the device and the needle is retracted to shield the needle. In one embodiment, the device includes a second port through which the guide wire is inserted while the fluid collection device is attached to the insertion device. The device may also include a shield configured for vascular insertion, which shields the needle after the needle is retracted.

28 Claims, 4 Drawing Sheets

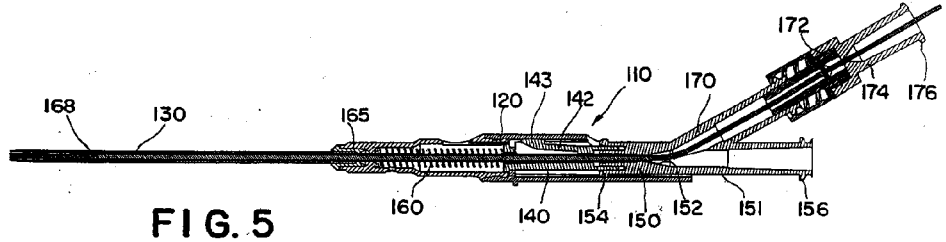

FIG. 5